(12) United States Patent
Taguchi et al.

(10) Patent No.: US 9,700,264 B2
(45) Date of Patent: Jul. 11, 2017

(54) JOINT ESTIMATION OF TISSUE TYPES AND LINEAR ATTENUATION COEFFICIENTS FOR COMPUTED TOMOGRAPHY

(71) Applicant: THE JOHNS HOPKINS UNIVERSITY, Baltimore, MD (US)

(72) Inventors: Katsuyuki Taguchi, Elkridge, MD (US); Kenji Amaya, Tokyo (JP); Kento Nakada, Tokyo (JP)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/519,356

(22) Filed: Oct. 21, 2014

(65) Prior Publication Data

US 2015/0131883 A1    May 14, 2015

Related U.S. Application Data

(60) Provisional application No. 61/895,542, filed on Oct. 25, 2013.

(51) Int. Cl.
*A61B 6/03* (2006.01)
*A61B 6/00* (2006.01)
*G06T 11/00* (2006.01)

(52) U.S. Cl.
CPC ............ *A61B 6/032* (2013.01); *A61B 6/4241* (2013.01); *A61B 6/5217* (2013.01); *G06T 11/006* (2013.01); *G06T 2211/408* (2013.01)

(58) Field of Classification Search
CPC ...... G06T 11/005; A61B 6/032; A61B 6/4241
(Continued)

(56) References Cited

U.S. PATENT DOCUMENTS 5,859,891 A * 1/1999 Hibbard ............... G06T 7/0012
378/62
6,950,493 B2    9/2005 Besson
(Continued)

FOREIGN PATENT DOCUMENTS

EP          2054856 B1    10/2010
WO          9409383 A1     4/1994
(Continued)

OTHER PUBLICATIONS

Gallagher, Marcus, et al. "Bayesian inference in estimation of distribution algorithms." Evolutionary Computation, 2007. CEC 2007. IEEE Congress on. IEEE, 2007. Month: Sept.*
(Continued)

*Primary Examiner* — Amandeep Saini
(74) *Attorney, Agent, or Firm* — Johns Hopkins Technology Ventures

(57) ABSTRACT

The present invention is directed to a new joint estimation framework employing MAP estimation based on pixel-based latent variables for tissue types. The method combines the geometrical information described by latent MRF, statistical relation between tissue types and P-C coefficients, and Poisson noise models of PCD data, and makes possible the continuous Baysian estimation from detected photon counts. The proposed method has better accuracy and RMSE than the method using FBP and thresholding. The joint estimation framework has the potential to further improve the accuracy by introducing more information about tissues in human body, e.g., the location, size, and number of tissues, or limited variation of neighboring tissues, which will be easily formulated by pixel-based latent variables.

19 Claims, 11 Drawing Sheets

(58) Field of Classification Search
USPC .......................................................... 382/131
See application file for complete search history.

(56) References Cited

U.S. PATENT DOCUMENTS

| | | | |
|---|---|---|---|
| 6,973,158 B2 | 12/2005 | Besson | |
| 7,116,749 B2 | 10/2006 | Besson | |
| 8,532,744 B2 | 9/2013 | Das et al. | |
| 2008/0063135 A1* | 3/2008 | DeMan | A61B 6/032 378/4 |
| 2010/0135453 A1* | 6/2010 | Mendonca | A61B 6/032 378/5 |
| 2011/0064291 A1* | 3/2011 | Kelm | G06T 7/0087 382/131 |
| 2014/0046894 A1* | 2/2014 | Bradley | G06N 5/02 706/52 |

FOREIGN PATENT DOCUMENTS

| | | |
|---|---|---|
| WO | 2009060351 A1 | 5/2009 |
| WO | 2009102996 A2 | 8/2009 |

OTHER PUBLICATIONS

Alessio, A., et al., "Quantitative material characterization from multienergy photon counting CT", Medical Physics, (2013), vol. 40, No. 3.

Schirra, C., et al., "Statistical Reconstruction of Material Decomposed Data in Spectral CT", IEEE Transaction of Medical Imaging, (Jul. 2013), vol. 32, No. 7.

Wang, X., et al., "Material separation in x-ray CT with energy resolved photon-counting detectors", Medical Physics, (Mar. 2011), vol. 38, No. 3.

* cited by examiner

TISSUE TYPES

CT NUMBER

PHOTOELECTRIC COEFFICIENT

COMPTON SCATTERING COEFFICIENT

CHARACTERISTIC COEFFICIENTS

ROI OF ADIPOSE

HORIZONTAL PROFILE REGION
FOR FWHM

INPUT: $\hat{Y}, \mu_k, \Sigma_k$ $(k = 1, ...K)$
OUTPUT: $Y^*, Z^*$
ESTIMATE $V_j, P_j$ FOR $j = 1, ..., J$;
INITIALIZE $W^0, Z^0$;
   $t = 0$;                                      /* ICM START */
WHILE $\Delta_p(W, Z | \hat{Y}) \geq \epsilon$ DO
   FOR $i = 1$ TO $N$ DO
      FOR $k = 1$ TO $K$ DO
         SOLVE $w_1^{NEW}|_{z_1^{(b)}=1} = \arg\min_{w_1} F(w_1^{(t)})|_{z_1^{(b)}=1}$
         ;                                       /* FIG. 2 (b) */
      END
      SELECT $(w_1^{(t+1)}, z_1^{(t+1)})$ FROM
         $w_1^{NEW}|_{z_1^{(b)}=1}$ $(k = 1, ..., K)$;  /* FIG. 2 (c) */
   END
   $t \leftarrow t+1$;                           /* FIG. 2 (d) */
END
RETURN $W, Z$;

FIG. 11

JOINT ESTIMATION OF TISSUE TYPES AND LINEAR ATTENUATION COEFFICIENTS FOR COMPUTED TOMOGRAPHY

CROSS REFERENCE TO RELATED APPLICATION

This application claims the benefit of U.S. Provisional Patent Application No. 61/895,542 filed on Oct. 25, 2013, which is incorporated by reference, herein, in its entirety.

FIELD OF THE INVENTION

The present invention relates generally to medical imaging. More particularly, the present invention relates to a method of tissue type estimation for use with computed tomography scanning.

BACKGROUND OF THE INVENTION

Energy sensitive photon counting detector-based, x-ray computed tomography (PCD-CT) has been one of the hottest research topics lately, as it is expected to provide various clinical benefits such as enhanced tissue contrast, decreased image noise, decreased radiation dose to patient, quantitative mono-energetic CT images, and more accurate material decomposition. Tissue types such as bones, fat, muscle, and iodine-enhanced blood can then be identified, allowing software applications to, e.g., separate blood vessels from bones, quantify the fat mass, etc.

The typical approach to process PCD data consists of the following two steps. First, by applying material decomposition, density images of basis functions (discussed later), w, are reconstructed from spectral projections, i.e., counts in multi-energy bins. Second, images of linear attenuation coefficients and tissue types are estimated from w.

This sequential method decouples the two steps and makes it difficult to use a priori information on tissue types to accurately estimate linear attenuation coefficients and tissue types from photon counts. For example, tissue types may be able to effectively regularize linear attenuation coefficients than a simple edge-preserving prior. The values of neighboring pixels of linear attenuation coefficients (and w) are expected to vary smoothly and continuously if they belong to the same tissue types, while they may be discontinuous at organ boundaries. The typical values of the chemical composition and mass density of various human tissue types or organs are provided by the National Institute of Standards and Technology, from which w and linear attenuation coefficients can be calculated.

Accordingly, there is a need in the art for a method to jointly estimate images of the energy-dependent linear attenuation coefficients and tissue types from PCD data.

SUMMARY OF THE INVENTION

The foregoing needs are met, to a great extent, by the present invention which provides a method for computed tomography imaging of a subject including obtaining photon counting detector-based x-ray computed tomography image information for the subject. The method includes performing material decomposition on the photon counting detector-based x-ray computed tomography image information for the subject. The method also includes assessing, simultaneously, an energy dependent linear attenuation coefficient and information about structures being imaged, and generating an image of the subject.

In accordance with an aspect of the present invention, the method includes reconstructing density images of basis functions, w. The method includes using latent Markov Random Field (MRF) calculations to describe geometrical information of the structures being imaged and w of the computed tomography image information for the subject. Additionally, the method includes determining a statistical relationship between a structure type and w. The method includes using Poisson noise models of PCD data and continuously executing a Bayesian estimation from a detected photon count. The method also includes programming a non-transitory computer readable medium to execute the method. The method includes w to represent a set of P-C coefficients on the image information, and using z to represent a set of latent variable labels. The method includes defining a prior distribution as a combination of the latent MRF and statistical distribution between w and z.

In accordance with another aspect of the present invention a non-transitory computer readable medium is configured for executing a method including obtaining photon counting detector-based x-ray computed tomography image information for the subject. The method includes performing material decomposition on the photon counting detector-based x-ray computed tomography image information for the subject. The method also includes assessing, simultaneously, an energy dependent linear attenuation coefficient and information about structures being imaged and generating an image of the subject.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIG. 11 illustrates an algorithm for a flow of JE-MAP.

DETAILED DESCRIPTION

Figure 1:
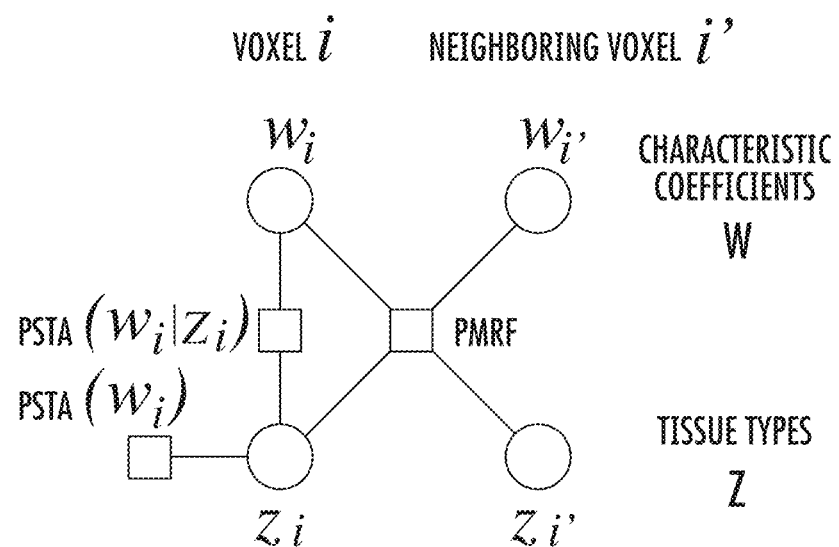
FIG. 1 illustrates a graphical view of a factor graph representing the voxel-based coupled MRF model and the Gaussian mixture model around voxel i.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

A method according to the present invention employs maximum a posteriori (MAP) Bayesian estimation based on pixel-based latent variables for tissue types: Poisson likelihood models PCD data; a Markov random field (MRF) represents the geometrical a priori information on tissue types and w; and the statistical a priori information relates tissue types and w. A computer simulation is performed to evaluate the effectiveness of the proposed method compared with the sequential, two-step method.

According to the present invention, a more accurate regularization can be performed with the knowledge of the tissue types and organ boundaries, and consequently, the image quality can be improved. The values of the linear attenuation coefficients for neighboring image pixels are expected to vary smoothly and continuously when they belong to the same tissue. In contrast, the values are usually discontinuous at the organ boundaries. Moreover, the typical values of the chemical composition and mass density of various human tissue types or organs are provided by the National Institute of Standards and Technology (NIST), from which expected values of linear attenuation coefficients can be calculated.

The present invention includes a novel image reconstruction method, denoted "Joint Estimation Maximum A Posteriori" (JE-MAP), which jointly estimates images of the energy-dependent linear attenuation coefficients and tissue types from PCD data using material decomposition. The method implements image reconstruction using prior information about tissue types as well as tissue type identification using information of the noise distribution during CT projection. The JE-MAP algorithm employs maximum a posteriori (MAP) estimation based on voxel-based latent variables for the tissue types. The geometrical and statistical information about human organs is incorporated as prior information using a voxel-based coupled Markov random field model and a Gaussian mixture model, respectively.

A. Problem Modeling

1) Characteristic Coefficients: The energy-dependent linear attenuation coefficients at photon energy E, x(E), can be described as a linear combination of the product of energy dependent basis functions, $\Phi_n(E)$ and their spatial distribution coefficients, $w_n$:

$$x(E) = \sum_{n=1}^{N_a} \omega_n \Phi_n(E), \tag{1}$$

$$\Phi(E) = \left( \frac{E^{-3}}{E_0^{-3}}; \frac{f_{KN}(\alpha)}{f_{KN}(\alpha_0)} \right)^T, \tag{2}$$

$$\omega = (\omega_{pe}, \omega_{cs})^T, \tag{3}$$

where $N_a=2$ is the number of basis functions, $E^{-3}$ denotes the photoelectric effect, $f_{KN}(\alpha)$ is the Klein-Nishina function for Compton scattering, $$f_{KN}(\alpha) = \frac{1+\alpha}{\alpha^2} \left\{ \frac{2(1+\alpha)}{1+2\alpha} - \frac{1}{\alpha}\ln(1+2\alpha) \right\} + \frac{1}{2\alpha}\ln 1 + 2\alpha - \frac{(1+3\alpha)}{(1+2\alpha)^2}, \tag{4}$$

where $\alpha = E/510.975$ keV; $\alpha_0 = E_0 = 510.975$ keV, and E0 is the reference energy. The coefficient vector w is denoted as the "characteristic coefficients". Note that it is straightforward to add a third basis function and the corresponding characteristic coefficients to describe the discontinuity at the K-edge of a contrast agent. However, it is assumed herein that large attenuation in the low X-ray energy range where the detected photon counts in the low energy bins are so small that the 'signal' of the K-edge effect is negligible.

2) Tissue Type Labeling: A goal is to estimate the characteristic coefficients and the tissue type for each image voxel from measured PCD sinogram data. Latent variable $z_i$ is introduced to express the tissue type at each image voxel i, i=1, ..., I, with I the total number of image voxels, using the Potts model represented by the 1-of-K scheme.

$$z_i \in \{(0,1)^K\}, \Sigma_{k=1}^K z_i^{(k)} = 1, \tag{5}$$

where $z_i^{(k)}$ represents the kth element of $z_i$ (k=1, ..., K). Thus, each image voxel is labeled by one of K tissue types with $z_i$.

3) Image and Projection Set Definition: Let i=1, ..., I be a voxel index of the tomographic image, and let W={$w_i$|i= 1, ..., I} represent a set of the characteristic coefficients in the tomographic image, and let Z={$z_i$|i=1, ..., I} be a set of the latent variables.

Furthermore, let j=1, ..., J be a sinogram pixel index, with J the total number of sinogram pixels, and let V={$v_i$|i=1, ..., I} be a set of line integrals of the characteristic coefficients in the sinogram, which can be calculated by forward projection of W as $$v_j = \Sigma_{i \in ray(j)} d_{ij} w_i \tag{6}$$

where ray(j) is a set of image voxels through which a ray goes to sinogram pixel j in the forward projection process, and $d_{ij}$ is an element of the forward projection matrix from image to sinogram. Let Y={$y_i$|i=1, ..., I} be a set of photon counts in the sinogram, where each pixel is given by $y_j = (y_{(j,1)}, ..., y_{(j,B)})$ which indicates the expected photon counts in B energy bins. The photon counts in each sonogram pixel $y_j$ can be calculated from $v_j$ as, $$y_{(j,b)} = h_b(v_j) = \int_{E_b}^{E_{b+1}} n(E) \exp(-v_j^T \Phi(E)) dE, \tag{7}$$

where b=1 ... B, n(E) denotes the x-ray spectrum emitted from the source described as a number of photon counts per keV, and the function $h_b: \mathbb{R}^{N_a} \to \mathbb{R}$ relates the line integral of the characteristic coefficients, v, to the expected photon counts through Eq. (1) and Beer's law. The set of measured photon counts in the sinogram is described by $\hat{Y}=\{\hat{y}_j|j=1,\ldots,J\}$ B. Cost Function The problem of image reconstruction, material decomposition, and tissue type identification can be formulated as a MAP estimation with W and Z as random variables whose estimates W*, Z* can be obtained by $$(W^*, Z^*) = \underset{W,Z}{\operatorname{argmin}}\{\ln p(\hat{Y}|W) - \ln p(W, Z)\}, \quad (8)$$

where p(Y|W) is the likelihood distribution of the measured data, and p(W, Z) is the likelihood of the prior distribution as explained in the following.

1) Likelihood: An ideal photon counting detector which is unaffected by pulse pileup effects or spectral response effects is assumed. Thus, the probability of photon counts in the bth energy bin at the jth pixel in the sinogram $\hat{y}_{(j,b)}$ follows a Poisson distribution as a result of the Poisson process of x-ray generation in the x-ray source and the binomial process of attenuation in the object. Therefore, the probability of PCD-CT measurements $\hat{Y}$ given the object is calculated by taking the product of each Poisson distribution for all the energy bins and sinogram pixels:

$$p(\hat{Y}|W) = \prod_{j=1}^{J}\prod_{b=1}^{B} \operatorname{Poisson}(\hat{y}_{(j,b)}|y_{(j,b)}) \quad (9)$$

2) Prior Distribution: We define the likelihood of the prior distribution as a combination of a voxel-based coupled Markov random field (MRF) model and a statistical distribution between W and Z, as illustrated in FIG. 1. FIG. 1 illustrates a graphical view of a factor graph representing the voxel-based coupled MRF model and the Gaussian mixture model around voxel i.

$$\ln p(W,Z) := \ln p_{MRF}(W,Z) + \ln p_{sta}(W,Z) \quad (10)$$

The voxel-based coupled MRF model formulates the relation between the characteristic coefficients w and the latent variable z between neighboring voxels, while a multivariate Gaussian mixture model describes the relation between w and z in each voxels.

Voxel-based Coupled MRF Model: To express the geometrical continuity and discontinuity of human organs, the coupled MRF model is used. The coupled MRF model consists of two MRFs, one for observable variables and the other for latent variables which describe the state of the voxels. The variances of the two MRFs are coupled to each other via a probability function, e.g., a conditional probability. We adopt the coupled MRF model with voxel-based latent variables (or a voxel-based coupled MRF), regarding characteristic coefficients as observable variables and tissue types as latent variables.

Let ne(i) be a set of indexes of neighboring voxels around image voxel i. Considering the Potts model of tissue types, the voxel-based coupled MRF model is designed as follows, $$-\ln p_{MRF}(W, Z) = \varepsilon(W, Z) + \ln C_{MRF}, \quad (11)$$

$$\varepsilon(W, Z) = \frac{1}{2}\sum_{i=1}^{I}\sum_{v \in ne(i)}\{\beta_1(z_i \cdot z_v)(w_i - w_v)^2 + \beta_2(1 - z_i \cdot z_v)\}, \quad (12)$$

where $\epsilon(W, Z)$ represents the energy function of the Gibbs distribution and $C_{MRF}$ is a normalization constant. If two tissue types $z_i$ and $z_{i'}$ are the same, then the inner product becomes $z_i \cdot z_{i'}=1$ and the first term of Eq. (12) encourages smoothness while the second term vanishes. When the tissue types are different then the first term vanishes and the second term adds a constant penalty. Two parameters, $\beta_1$ and $\beta_2$ control the effect of the two terms.

Gaussian Mixture Model: The statistical relationship between characteristic coefficients and tissue types are modeled. The expected values of w for various tissue types are obtained from the NIST database, and it is assumed that w follows a multivariate Gaussian distribution corresponded for each tissue type. The relationship between the w and all the tissue types is then modeled using a multivariate Gaussian mixture model, which is defined for each voxel.

For simplicity a tissue type is denoted expressed by the latent variable $z_i^{(k)}=1$ as the "kth tissue type". In the Gaussian mixture model, the probability of $z_i$ can be described by using mixing coefficients $\pi_k$ as $$p_{sta}(z_i^{(k)}=1)=\pi_k, \quad (13)$$

$$0 \leq \pi_k \leq 1, \quad (14)$$

$$\sum_{k=1}^{K}\pi_k=1, \quad (15)$$

Because the Potts model is adopted, represented by the 1-of-K scheme for the latent variable z, Eq. (13) can be also written as $$p_{sta}(z_i) = \prod_{k=1}^{K}(\pi_k)^{z_i^{(k)}}, \quad (16)$$

The mixing coefficient $\pi_k$ represents prior information about the presence of a tissue type in each image voxel. Thus, $p_{sta}(z_i)$ can be formulated as, for example, a function of the location, size, or shape of the voxels that belong to a particular tissues type. For simplicity, we assume a uniform probability for all tissues, i.e., $p_{sta}(z_i)=1/K$ for all k.

The conditional probability of $w_i$ given $z_i$ is described as a multivariate Gaussian distribution:

$$p_{sta}(w_i|z_i^{(k)}=1)=N(w_i|\mu_k, \Sigma_k), \quad (17)$$

where $\mu_k$ and $\Sigma_k$ are the expected value and the covariance matrix of the characteristic coefficients for the kth tissue type, respectively. Using the notation of the Potts model, Eq. (17) can also be written as $$p_{sta}(w_i|z_i) = \prod_{k=1}^{K} N(w_i|\mu_k, \Sigma_k)^{z_i^{(k)}}, \quad (18)$$

Therefore, the multivariate Gaussian distribution of the statistical relation between W and Z can be obtained by summing the joint probabilities of Eq. (16) and Eq. (18) for all voxels:

$$-\ln p_{sta}(W,Z) = -\beta_3 \Sigma_{i=1}^{I} \{ \ln p_{sta}(z_i) + \ln p_{sta}(w_i|z_i) \} = \beta_3 \Sigma_{i=1}^{I} \{ \ln K + \Sigma_{k=1}^{K} z_i^{(k)} \{ \frac{1}{2}(w_i - \mu_k)^T \Sigma_k^{-1}(w_i - \mu_k) + \ln C_k \} \}, \quad (19)$$

where $C_k$ is the normalization constant of the multivariate Gaussian distribution for the kth tissue type, and $\beta_3$ is a weighting parameter.

TABLE I

DESCRIPTION OF NOTATIONS AND COMMONLY USED SYMBOLS HEREIN

| Symbol | Description |
|---|---|
| x | x-ray attenuation coefficient |
| y | photon counts, $y \in \mathbb{R}^{bin}$ |
| z | latent variable for tissue type, $z \in \{0, 1\}^K$ |
| w | characteristic coefficients, $w \in \mathbb{R}^{N_a}$ |
| v | projected characteristic coefficient, $v \in \mathbb{R}^{N_a}$ |
| μ | expected value of w for tissue types, $\mu \in \mathbb{R}^{N_a}$ |
| Σ | covariance matrix of w for tissue types, $\Sigma \in \mathbb{R}^{N_a \times N_a}$ |
| ν | expected value of v, $\nu \in \mathbb{R}^{N_a}$ |
| P | covariance matrix of v, $P \in \mathbb{R}^{N_a \times N_a}$ |

C. Optimization

The MAP estimation Eq. (8) is computationally intractable due to the nonlinearity of x-ray attenuation and the introduction of latent variables. Therefore, the likelihood in Eq. (9) is approximated by a Gaussian distribution, and an iterated conditional modes (ICM) algorithm is used, which realizes voxel-driven optimization with the discrete latent variables. The flowchart of the JE-MAP algorithm is summarized in the pseudo code in FIG. 11.

FIG. 11 shows a flow of JE-MAP. First, the likelihood approximation is performed followed by initializing the image set of characteristic coefficients and tissue types. Because latent variable for tissue types are introduced, the cost function tends to have more local minima than the method regarding only characteristic coefficients as variables. The ICM is terminated when the difference in the cost function from one iteration to the next becomes less than a certain value ϵ.

1) Approximation of the Likelihood: For a given set of latent variables Z, both prior terms in Eqs. (11) and (19) are quadratic functions of w. The Poisson likelihood term, Eq. (9), however, is not quadratic and expensive to compute. Thus, the Poisson likelihood is approximated by a Gaussian distribution of the line integrals of the characteristic coefficients, V.

Using Eq. (6), the likelihood function of W given $\hat{Y}$ to the likelihood function of V given $\hat{Y}$ as, $$p(\hat{Y}|W) = L(W|\hat{Y}) = L(V|\hat{Y}) = \Pi_{j=1}^{J} L(v_j|\hat{y}_j). \quad (20)$$

The transformation between W and V satisfies the data sufficiency, i.e., the mapping q: W→V is bijective. The Poisson likelihood L can be written as follows using the function $h_b$ in Eq. (7).

$$L(v_j|\hat{y}_j) = \prod_{b=1}^{B} \frac{h_b(v_j)^{\hat{y}_{(j,b)}} \exp(-h_b(v_j))}{\hat{y}_{(j,b)}!}. \quad (21)$$

This likelihood function is approximated with a multivariate Gaussian distribution, $$L(v_j|\hat{y}_j) \approx N(v_j|v_j^*, P_j^*), \quad (22)$$

where $v_j^* \in \mathbb{R}^{N_a}$ and $P_j^* \in \mathbb{R}^{N_a \times N_a}$ are the mean vector and covariance matrix, respectively, of the line integrals of the characteristic coefficients. The parameters are found by minimizing the Kullback-Leibler divergence of the multivariate Gaussian distribution with constant factor N from the likelihood L:

$$(v_j^*, P_j^*) = \arg_{v_j, P_j} \min D_{KL}(L\|N), \quad (23)$$

$$D_{KL}(L\|N) = \int \ln\left(\frac{L(v_j|\hat{y}_j)}{N(v_j|v_j, P_j)}\right) L(v_j|\hat{y}_j) dv_j. \quad (24)$$

As shown in Appendix A, the minimum is given by $$v_j^* = \frac{\int L(v_j|\hat{y}_j) v_j dv_j}{\int L(v_j|\hat{y}_j) dv_j}, \quad (25)$$

$$P_j^* = \frac{\int L(v_j|\hat{y}_j) v_j v_j^T dv_j}{\int L(v_j|\hat{y}_j) dv_j} - v_j^* v_j^{*T}. \quad (26)$$

By performing the minimization for sinogram pixels $j=1, \ldots, J$ independently, the Gaussian parameters for the entire sonogram are obtained. The Poisson likelihood of the image W given the measurement $\hat{Y}$ is approximated by multivariate Gaussian distributions of $v_j$ given the parameters $v_j^*$ and $P_j^*$:

$$p(\hat{Y}|W) \approx \Pi_{j=1}^{J} N(v_j|v_j^*, P_j^*). \quad (27)$$

Figure 2:
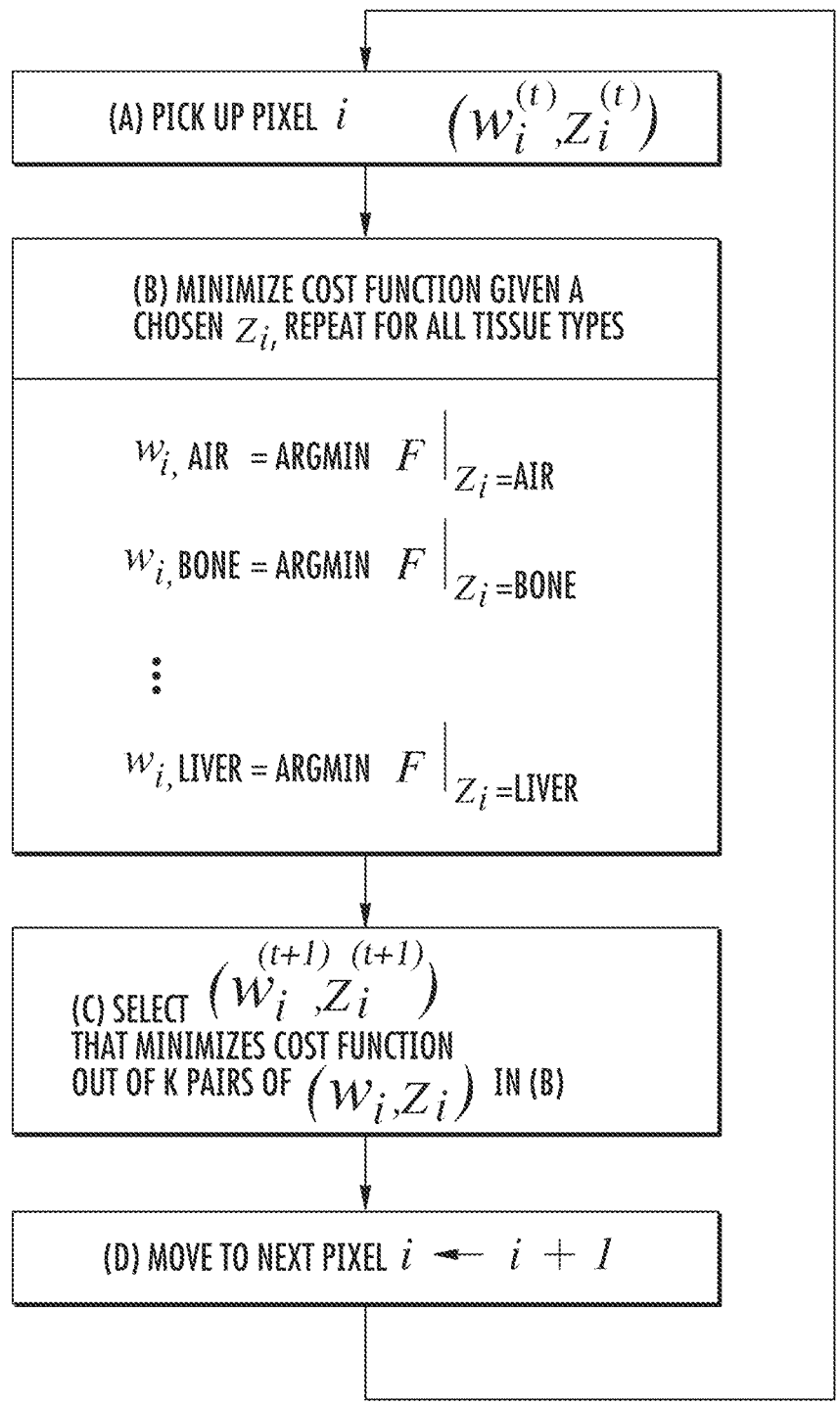
FIG. 2 illustrates a schematic diagram of a core scheme of the ith iteration of ICM. The ith iteration ends when the flow (a) to (c) is completed for all voxels.

2) Iterative Method: In order to handle all of the combinations of discrete variables z efficiently, an iterated conditional modes (ICM) algorithm was used, which updates the parameters of each image voxel successively. The flowchart of ICM as used in the JE-MAP algorithm is shown in FIG. 2. FIG. 2 illustrates a schematic diagram of a core scheme of the ith iteration of ICM. The ith iteration ends when the flow (a) to (c) is completed for all voxels.

During the update of the ith voxel in the tth iteration, the following sub-minimization of the quadratic cost function $F(w_i)$ is performed with $z_i$ fixed to one of the K tissue types:

$$w_i^{new}|_{z_i^{(k)}=1} = \arg_{w_i} \min F(w_i)|_{z_i^{(k)}=1}, \quad (28)$$

$$F(w_i)|_{z_i^{(k)}=1} = \sum_{j \in ray'(i)} g_j(w_i)^T P_j^{-1} g_j(w_i) + \quad (29)$$

$$\sum_{v \in ne(i)} \{\beta_i(z_1 \cdot z_2)(w_i - w_v)^2 + \beta_2(1 - z_i \cdot z_d)\} +$$

$$\beta_3 \left\{ (w_t - \mu_k)^T \sum_k (w_i - \mu_k) + C_k \right\},$$

$$g_j(w_i) = d_{ij}(w_i - w_i^{(t)}) - (v_j - v_j^{(t)}), \quad (30)$$

where ray'(i) denotes a set of sinogram pixels onto which the voxel i is projected, and the constant values $w_i^{(t)}$ and $v_j^{(t)}$ are characteristic coefficients of image voxel i and the line integral of characteristic coefficients in sinogram pixel j, respectively, both of which were estimated in the previous (t−1)th iteration.

Because the cost function $F(w_i)$ is convex and quadratic over $w_i$ in each sub-minimization as shown in Appendix B, its minimum can be analytically found with no iteration by completing the square. After performing the sub-minimization procedure for all K tissue types, the characteristic coefficients $w_i^{new}$ and tissue type $z_i^{new}$ which give the minimum cost are selected and used in the next step.

III. EXEMPLARY IMPLEMENTATIONS

Exemplary implementation of the present invention are described herein, in order to further illustrate the present invention. The exemplary implementation is included merely as an example and is not meant to be considered limiting. Any implementation of the present invention on any suitable subject known to or conceivable by one of skill in the art could also be used, and is considered within the scope of this application.

A. Phantom and Scan

Figure 3A:
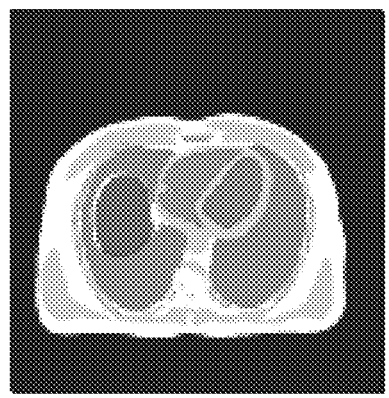
FIGS. 3A-3E illustrate images and graphical data related to a thorax of the modified XCAT phantom.
Figure 3B:
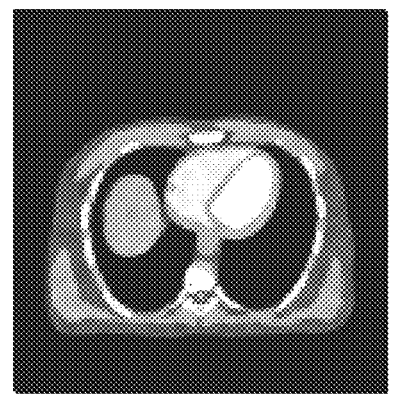
Figure 3C:
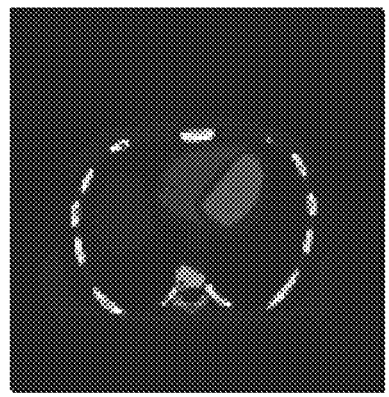
Figure 3D:
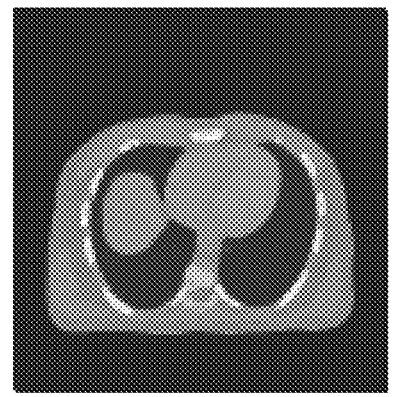
Figure 3E:
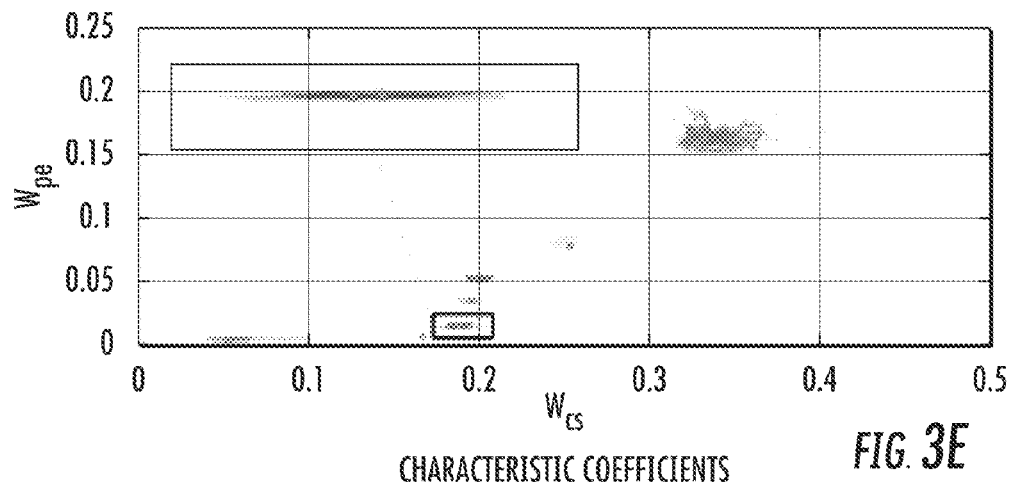

A modified thorax image of the XCAT phantom was used with the nine tissue types shown in FIG. 3A. FIGS. 3A-3E illustrate images and graphical data related to a thorax of the modified XCAT phantom. FIG. 3A illustrates an image of nine tissue types including air indicated by different shading. FIG. 3B illustrates a monochromatic CT image at 70 keV, WW 600 HU and WL 0 HU. FIGS. 3C and 3D illustrate images of distributions of two character coefficients. FIG. 3E illustrates a graphical view of a scatter plot of characteristic coefficients in the phantom. The phantom image covered 40×40 cm² by 512×512 pixels, and geometrical textures were added to make the image pixel values inside organs heterogeneous. Parallel beam projections were simulated with Poisson noise and the following parameters: tube voltage 140 kV, x-ray $10^5$ counts per incident projection ray, 360 projections over 180°, 728 detectors with 0.78125 mm width, and 4 energy thresholds at 10, 40, 70, 100 keV. 100 noise realizations were performed.

B. Reconstruction and Tissue Type Classification

First, material decomposition was performed to obtain two sinograms of the characteristic coefficients from the PCD data through Eq. (20) to Eq. (26). Then, images of the characteristic coefficients were reconstructed using the following three methods: FBP, PML, and JE-MAP. A color table for tissue types in the phantom is included below. The FBP images were used as an initial estimate for PML and JE-MAP. For each image pixel, a tissue type is chosen which gives the minimum L2-norm distance from the statistically expected values to the image pixel value. FBP with a Shepp-Logan filter was performed on each of the three sinograms of the characteristic coefficients independently to obtain the corresponding image.

TABLE II

COLOR TABLE FOR TISSUE TYPES IN THE PHANTOM

| tissue type | color name |
|---|---|
| air | black |
| muscle | green |
| lung | brown |
| spine | light gray |
| rib | dark gray |
| adipose | yellow |
| liver | blue |
| blood w/0.8% Iodine | light magenta |
| blood w/0.4% Iodine | dark magenta |

PML minimizes the Gaussian likelihood of the data (Eq. (22)) with a quadratic regularizer R(W) weighted by $\gamma=5\times 10^4$:

$$W^*=\arg_W \max\{\ln p(\hat{Y}|W) - \ln R(W)\},$$
$$R(W) = 1/2 \sum_{i=1}^{N} \sum_{v \in ne(i)} \gamma (w_i - w_v)^2. \quad (31)$$

JE-MAP was performed with $\beta_1=6.0\times 10^4$, $\beta_2=1.5$, and $\beta_3=1.0$. The covariance matrix $\Sigma_k$ was sampled from the phantom and scaled by $\beta_4=1.0\times 10^{-2}$.

$$\Sigma_k = \beta_4 \Sigma_{sample,k}. \quad (32)$$

For each image pixel of $w_i$ a tissue type is chosen which gives the minimum L2-norm distance from the statistically expected values to the image pixel value. Monochromatic CT images at 70 keV were synthesized from the characteristic coefficient images using Eq. (1).

C. Impact of Parameters

In order to better understand the role of the four terms in JEMAP, only one of the four parameters, $\beta_1$, $\beta_2$, $\beta_3$, $\beta_4$ was changed at a time and qualitatively evaluated the image quality.

D. Quantitative Evaluation

The standard deviation, σ, of pixel values over 100 noise realizations was measured. The averaged value over adipose regions shown in FIG. 4A was used to measure the image noise.

Figure 4A:
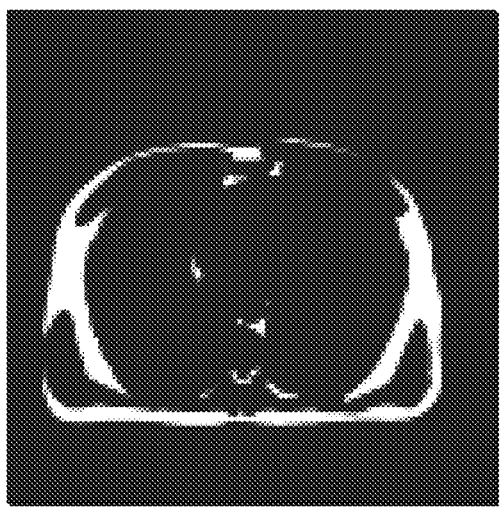
FIGS. 4A and 4B illustrate images where the mean of the standard deviation is obtained in the inner region of adipose in FIG. 4A and illustrates an image where the FWHMs are calculated from horizontal edges inside the region indicated by the white box in FIG. 4B.
Figure 4B:
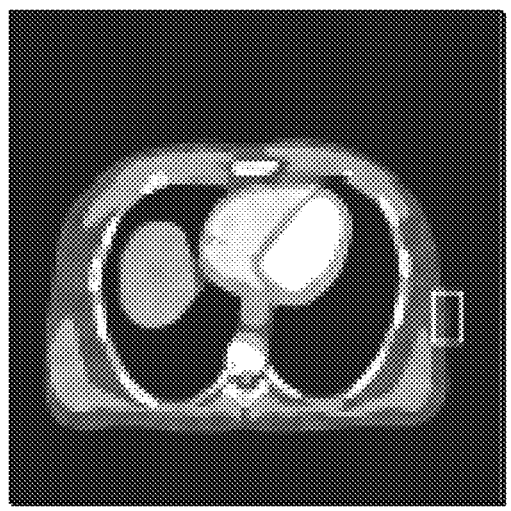

The spatial resolution was quantified by fitting an error function to each horizontal edge profile in the region shown in FIG. 4B.

$$\text{Edge}(x) = \frac{\lambda_1}{2}\left(1 + \text{erf}\left(\frac{x - \lambda_2}{\sqrt{2}\lambda_3}\right)\right) + \lambda_4, \quad (33)$$

In Eq. (33), $\lambda_3$ indicates the sharpness of the edge, from which the full-width-at-half-maximum (FWHM) was calculated as FWHM=$2\sqrt{2\ln 2}\lambda_3$. The FWHM was averaged over all profiles to obtain a measure for the spatial resolution. The trade-off between the image noise and spatial resolution was obtained by applying different Gaussian filters to the images and repeating the measurements.

The accuracy of the CT images was quantified by calculating the bias of the monochromatic CT images for each pixel, and the mean bias was calculated over the entire region inside the phantom. The accuracy of the tissue types was assessed in a binary fashion on a pixel basis. When the chosen tissue type for the image pixel was the correct tissue type, it was considered an accurate outcome; if it was not the correct tissue type, it was considered an inaccurate outcome. The ratio of the number of accurate outcomes to the number of image pixels is the accuracy of the tissue types.

FIGS. 4A and 4B illustrate images where the mean of the standard deviation is obtained in the inner region of adipose in FIG. 4A and illustrates an image where the FWHMs are calculated from horizontal edges inside the region indicated by the white box in FIG. 4B.

IV. EVALUATION RESULTS

Figure 5A:
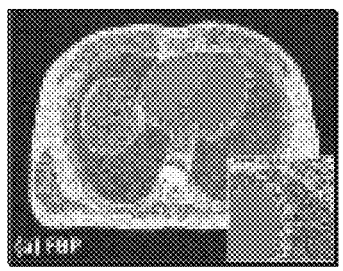
FIGS. 5A-5F illustrate the estimated tissue types and monochromatic CT images at 70 keV from one noise realization.
Figure 5B:
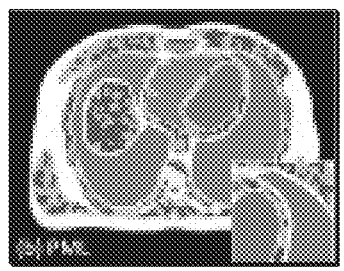
Figure 5C:
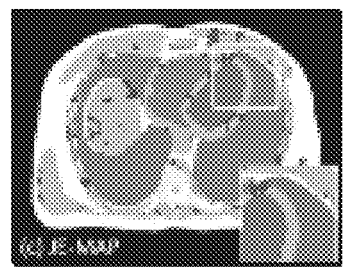
Figure 5D:
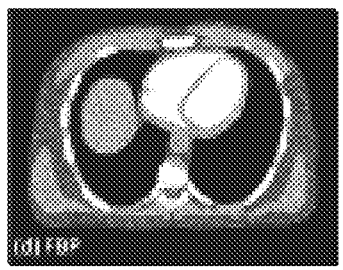
Figure 5E:
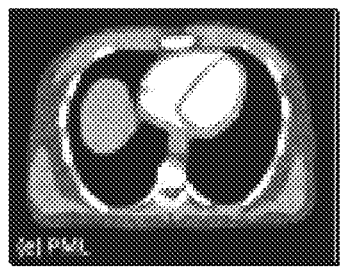
Figure 5F:
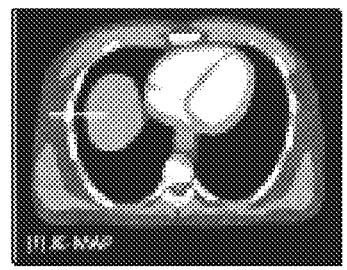
Figure 6:
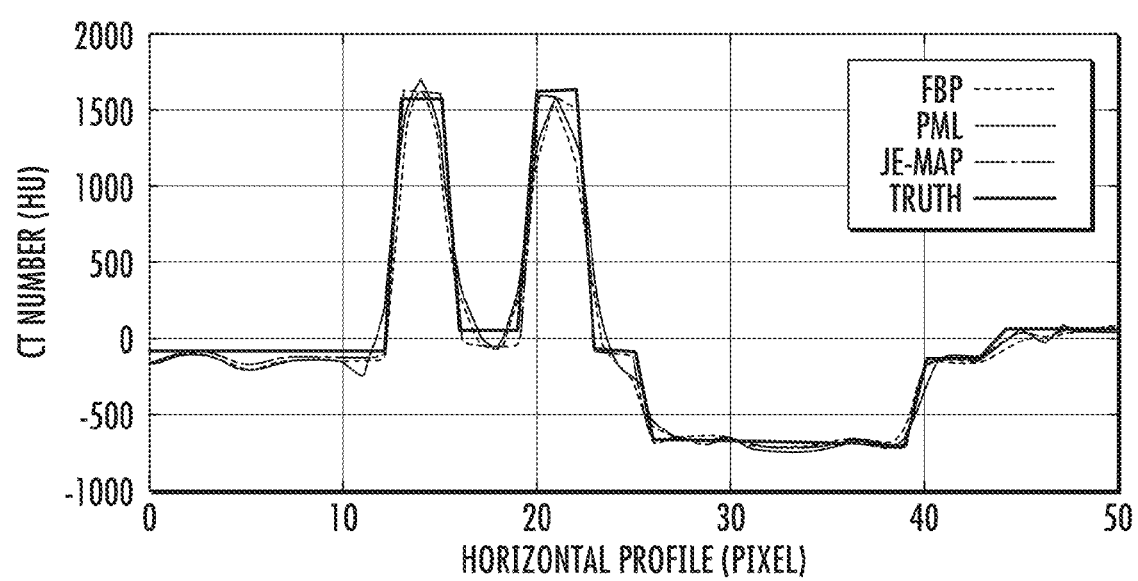
FIG. 6 illustrates a graphical view of a horizontal profile take along the line shown in FIG. 5F for each reconstruction method through adipose, rib, lung, and a thin layer of adipose, and the liver.

FIGS. 5A-5F illustrate the estimated tissue types and monochromatic CT images at 70 keV from one noise realization and FIG. 6 illustrates a graphical view of a horizontal profile take along the line shown in FIG. 5F for each reconstruction method through adipose, rib, lung, and a thin layer of adipose, and the liver. More particularly, FIGS. 5A-5C illustrate images of estimated tissue types and FIGS. 5D-5F illustrate monochromatic CT images at 70 keV (WW 600 HU, WL 0 HU). A strong salt and pepper noise can be seen in the FBP image (σ=46.8 HU in entire phantom) which resulted in a salt and pepper pattern in the tissue type image as well. PML provided CT images with less noise (σ=38.5 HU). However, it blurred the organ boundaries as shown in FIG. 6, which resulted in wrong tissue type identification near the organ boundaries. For example, it can be seen that there is adipose tissue identified at the boundaries between the heart muscle and the lung, or the heart muscle and the ventricles. JE-MAP reconstructed CT images with much less noise (σ=27.4 HU), while the boundaries of organs remained sharp (FIG. 6) resulting in more accurate tissue type identification at the boundaries. There are some regions in the tissue images of PML and JE-MAP where muscle and liver tissues were mislabeled because the characteristic coefficients of muscle and liver are too close to each other to be separated (see FIG. 3E).

Figure 7A:
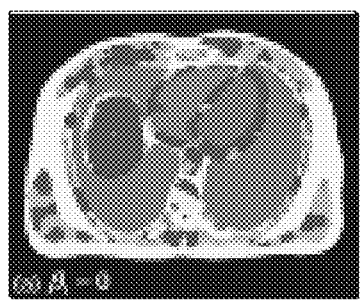
FIGS. 7A-7F illustrate JE-MAP images when one of the four parameters was smaller than the default setting used in FIGS. 5A-5F.
Figure 7B:
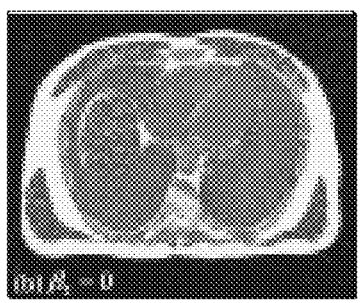
Figure 7C:
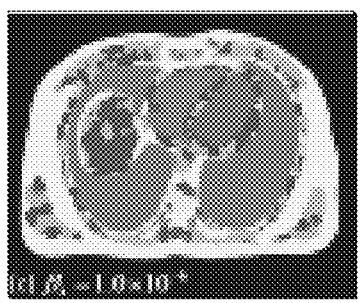
Figure 7D:
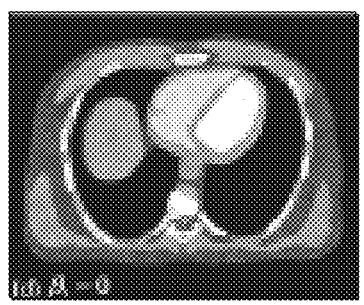
Figure 7E:
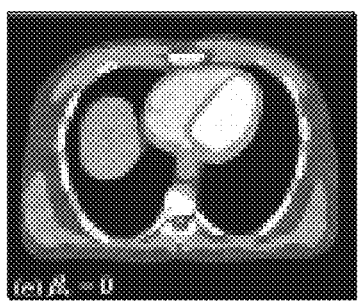
Figure 7F:
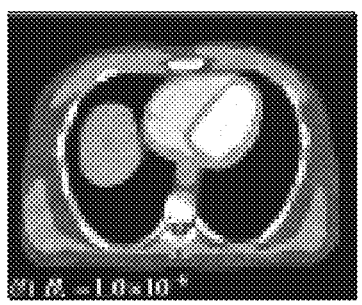

FIGS. 7A-7F illustrate JE-MAP images when one of the four parameters was smaller than the default setting used in FIGS. 5A-5F. FIGS. 7A-7C illustrate images of estimated tissue types. FIGS. 7D-7F illustrate images of monochromatic CT images at 70 keV obtained by JE-MAP with smaller parameters than the optimal ones. (WW 600 HU, WL 0 HU). FIGS. 7A and 7D are taken with a smaller $\beta_1$, FIGS. 7B and 7E taken with a smaller $\beta_2$, and FIGS. 7B and 7E also taken with a smaller $\beta_4$.

Figure 8A:
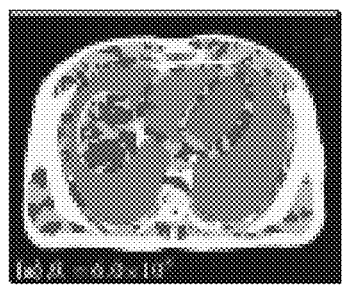
FIGS. 8A-8F illustrate images with larger parameters than optimal used in FIGS. 5A-5F.
Figure 8B:
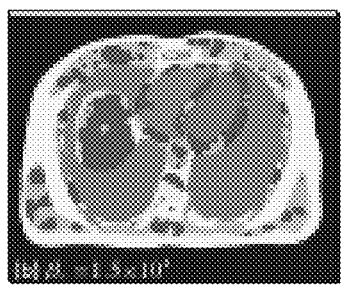
Figure 8C:
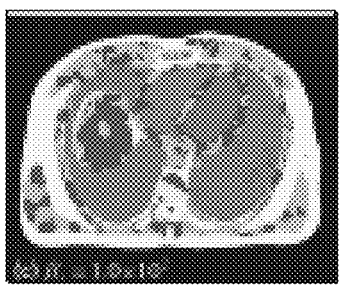
Figure 8D:
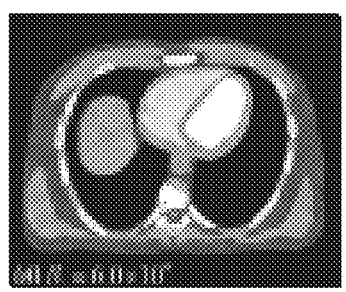
Figure 8E:
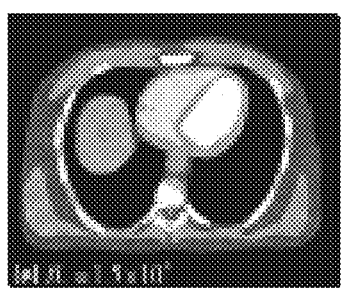
Figure 8F:
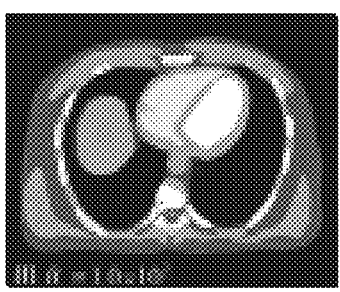

FIGS. 8A-8F illustrate images with larger parameters than optimal used in FIGS. 5A-5F. FIGS. 8A-8C illustrate images of the estimated tissue types, and FIGS. 8D-8F illustrate monochromatic CT images at 70 keV obtained by JE-MAP with larger parameters than the optimal ones. (WW 600 HU, WL 0 HU). FIGS. 8A and 8D are taken with a smaller $\beta_1$, FIGS. 8B and 8E taken with a smaller $\beta_2$, and FIGS. 8B and 8E also taken with a smaller $\beta_4$. The use of a smaller $\beta_1$ made the images heterogeneous but noisy (FIGS. 7A and 7D), while the use of a larger $\beta_1$ resulted in a camouflage pattern caused by mislabeled tissue types (FIGS. 8A and 8D). Decreasing $\beta_2$ resulted in salt and pepper noise (FIGS. 8B and 8E), while increasing $\beta_2$ made the shape of the organs smoother (FIGS. 8B and 8E)). Both $\beta_3$ and $\beta_4$ had the same effect on the images, and decreasing either $\beta_3$ or $\beta_4$ weakened the relationship between the characteristic coefficients so that the pixels were identified as either tissue type. Increasing either $\beta_3$ or $\beta_4$ made the characteristic coefficients (thus, CT pixel values) to be closer to the statistically expected values, suppressing the geometrical heterogeneous textures inside the organs.

Figure 9A:
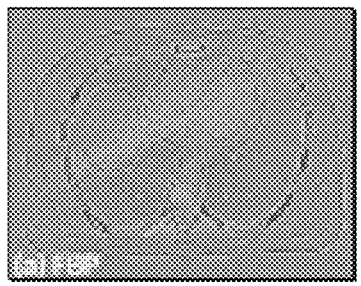
FIGS. 9A-9C illustrate image results of 100 noise realizations with bias.
Figure 9B:
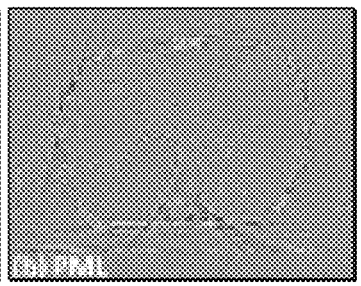
Figure 9C:
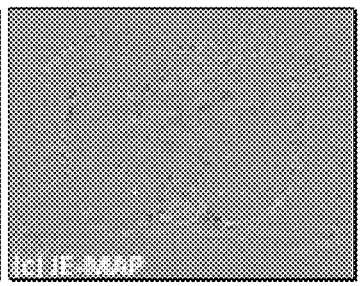
Figure 9D:
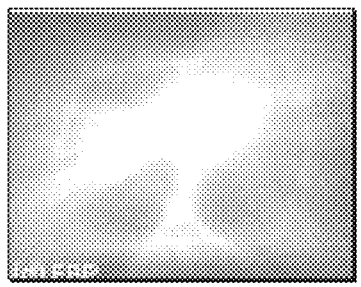
FIGS. 9D-F illustrate image results of 100 noise realizations with noise of CT images.
Figure 9E:
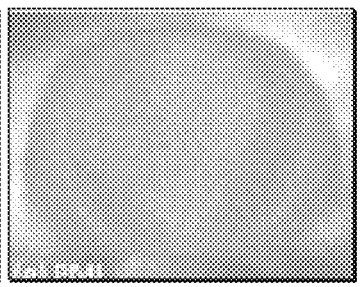
Figure 9F:
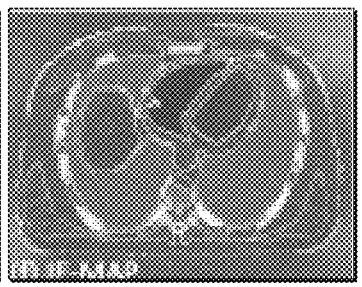
Figure 9G:
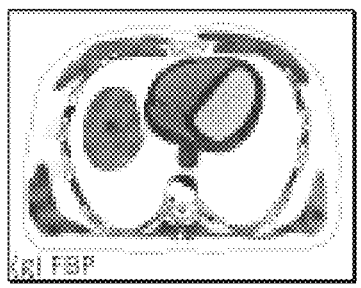
FIGS. 9G-9I illustrate image results of 100 noise realizations with the accuracy of tissue type identification.
Figure 9H:
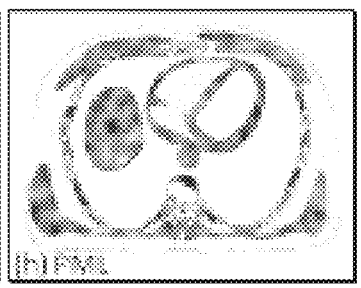
Figure 9I:

FIGS. 9A-9C illustrate image results of 100 noise realizations with bias. FIGS. 9D-F illustrate image results of 100 noise realizations with noise of CT images, and FIGS. 9G-9I illustrate image results of 100 noise realizations with the accuracy of tissue type identification. Display window width and level are: (9A-9C) 100 HU, 0 HU, (9D) 100 HU, 100 HU, (9E-9F) 30 HU, 60 HU, (9D) 100 HU, 100 HU, and (9G-9I) 50%, 100%.

Figure 10:
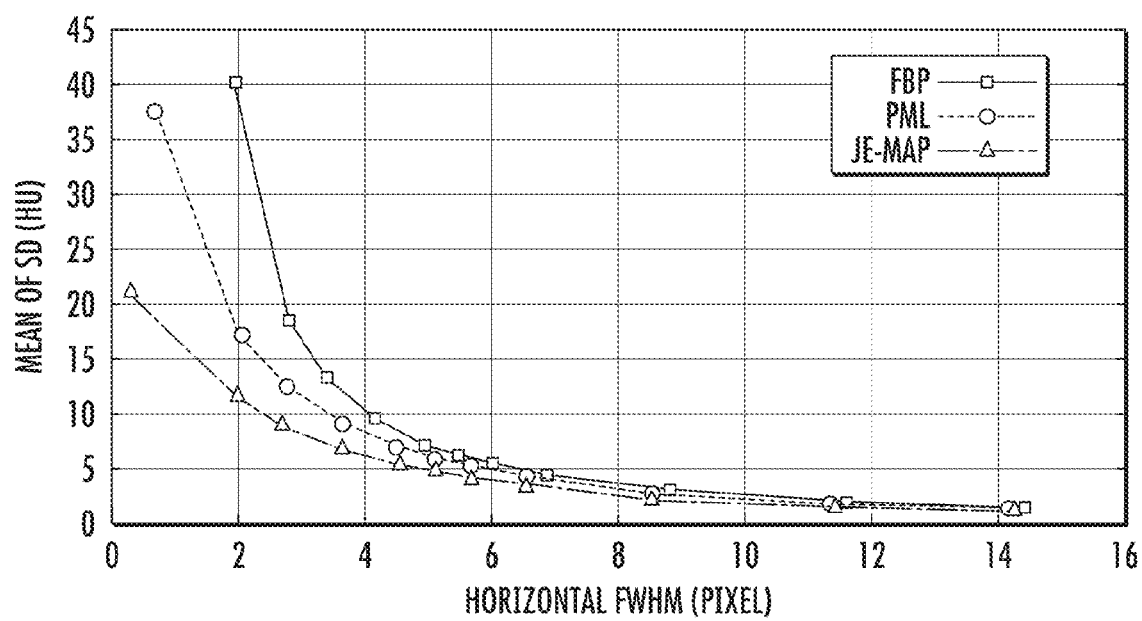
FIG. 10 illustrates a graphical view of noise-resolution tradeoff curves.

FIGS. 9A-9I illustrate the bias and standard deviation of the CT images at 70 keV, and the accuracy of the tissue type identification. The mean values were measured for each organ excluding pixels near the boundaries of organs and are presented together with the mean values of the entire phantom in Tables III, IV, and V, below. It can be seen that JE-MAP provided the best values in most indexes. The bias was as small as −0.1 HU with JE-MAP. The image noise of the entire phantom (Table IV) was 46.8 HU for FBP, 38.5 HU for PML and 27.4 HU for JE-MAP. The accuracy of tissue types improved from 71.7% for FBP and 80.1% for PML to 86.9% for JE-MAP. The low accuracy of muscle with JE-MAP was attributed to the mislabeling as liver. The resolution-noise tradeoff curves were shown in FIG. 10, where the top-left end-point of the curves was obtained from the images reconstructed by the corresponding method. JE-MAP provided the best tradeoff performance. FIG. 10 illustrates a graphical view of noise-resolution tradeoff curves. The top-left point of each method is the values from the estimated images, and the curves are obtained by blurring each image with a Gaussian filter with various parameters.

TABLE III

MEAN BIAS IN HOMOGENEOUS TISSUE REGIONS

| | Bias (HU) | | |
|---|---|---|---|
| tissue type | FBP | PML | JE-MAP |
| air | 0.1 | 0.0 | 0.0 |
| muscle | 1.0 | 0.3 | 0.3 |
| lung | −1.0 | −0.1 | 0.0 |
| spine | 6.2 | −0.6 | −0.4 |
| rib | −1.0 | 46.8 | 3.4 |
| adipose | 0.0 | 0.2 | 0.0 |
| liver | 2.6 | 0.5 | 0.0 |
| blood w/0.8% Iodine | 3.5 | 0.6 | 0.4 |
| blood w/0.4% Iodine | 4.4 | 0.6 | −0.3 |
| Entire phantom | −1.8 | −0.9 | −0.1 |

TABLE IV

MEAN STANDARD DEVIATION IN HOMOGENEOUS TISSUE REGIONS

| | Standard deviation (HU) | | |
|---|---|---|---|
| tissue type | FBP | PML | JE-MAP |
| air | 28.0 | 34.9 | 23.6 |
| muscle | 46.2 | 38.4 | 21.6 |
| lung | 43.1 | 37.8 | 24.3 |
| spine | 56.5 | 39.9 | 26.8 |
| rib | 49.1 | 39.4 | 38.8 |
| adipose | 39.9 | 37.9 | 21.2 |
| liver | 59.9 | 39.0 | 20.4 |
| blood w/0.8% Iodine | 63.3 | 39.9 | 16.5 |
| blood w/0.4% Iodine | 64.0 | 39.9 | 18.8 |
| Entire phantom | 46.8 | 38.5 | 27.4 |

TABLE V

MEAN ACCURACY IN HOMOGENEOUS TISSUE REGIONS

| | Accuracy (%) | | |
|---|---|---|---|
| tissue type | FBP | PML | JE-MAP |
| air | 99.9 | 100.0 | 100.0 |
| muscle | 34.3 | 49.7 | 54.6 |
| lung | 98.1 | 100.0 | 100.0 |
| spine | 99.6 | 100.0 | 100.0 |
| rib | 100.0 | 100.0 | 99.8 |
| adipose | 94.1 | 94.0 | 100.0 |
| liver | 41.9 | 52.8 | 91.6 |
| blood w/0.8% Iodine | 41.4 | 90.5 | 100.0 |
| blood w/0.4% Iodine | 68.4 | 95.0 | 100.0 |
| Entire phantom | 71.7 | 80.1 | 86.9 |

V. DISCUSSION AND CONCLUSION

The present invention is directed to a new framework, JE-MAP, to jointly perform image reconstruction, material decomposition, and tissue type identification for photon-counting x-ray CT. The results showed that JE-MAP provided superior noise-resolution tradeoff for the CT images (FIG. 10) than PML with quadratic penalty and FBP. This is because JE-MAP does not penalize differences between adjacent pixels at organ boundaries, while PML with quadratic penalty encourages smoothness even at edges. A PML with edge-preserving penalty could perform better than that with quadratic penalty, and a comparison with JE-MAP would be of interest. However, JE-MAP has a greater potential than PML, because an edge-preserving penalty such as the Huber penalty changes the strength of the penalty based on differences in pixel values, which are affected by image noise. Moreover, JE-MAP could use more prior information about tissues in the human body via additional latent variables such as the location, the size, and the number of pixel groups with the same tissue type.

The accuracy of the tissue type identification improved as well for JE-MAP compared to PML and FBP. While the tissue type images based on FBP and PML images showed an isolated salt-and-pepper noise pattern, JE-MAP provided pixels with the same tissue type grouped together to form 'islands.' This is because JE-MAP honors the statistical relation between the characteristic coefficients and the tissue types and those between neighboring pixels. Another advantage of JE-MAP is that the tissue-type identification is based on the projection likelihood rather than on information from image voxels. This means that JE-MAP can perform identification by placing more weight on the prior information if the reconstructed characteristic coefficients are not accurate due to large noise in the projection data.

A potential problem of JE-MAP with the current parameter setting is that it might suppress heterogeneous textures inside organs (FIG. 9C) or introduce a bias. This behavior can be attributed to suboptimal parameters such as $\beta_4$. A larger $\beta_4$ decreases the image noise as can be seen in FIG. 8F, but at the expense of heterogeneous texture and bias.

APPENDIX

A. Derivation of Equation (25), (26)

In this section the analytic solution for the minimization of the Kullback-Leibler divergence of a multivariate Gaussian distribution is presented. The minimization of the Kullback-Leibler divergence over the expected vector $v_j$ and covariance matrix $P_j$ of the multivariate Gaussian distribution can be described by extracting the terms including $v_j$ and $P_j$ as, $$(v_j^*, P_j^*) = \arg_{v_j, P_j} \min G(v_j, P_j), \quad (34)$$

$$G(v_j, P_j) = \int L(v_j | \hat{y}_j)\{(v_j - v_j)^T P_j^{-1}(v_j - v_j) - \ln|P_j^{-1}|\} dv_j. \quad (35)$$

The values $v_j^*$, $P_j^*$ that minimize the Kullback-Leibler divergence are those where partial derivatives equal zero.

$$\frac{\partial G}{\partial v_j} = 0 \Rightarrow \text{Eq. 25} \quad (36)$$

$$\left.\frac{\partial G}{\partial P_j}\right|_{v_j = v_j^*} = 0 \Rightarrow \left.\frac{\partial G}{\partial P_j^{-1}}\right|_{v_j = v_j^*} = \quad (37)$$

$$0 \Rightarrow \int L(v_j | \hat{y}_j) v_j v_j^T dv_j - 2v_j^* \int L(v_j | \hat{y}_j) v_j^T dv_j +$$

$$v_j v_j^* \int L(v_j | \hat{y}_j) dv_j - P_j \int L(v_j | \hat{y}_j) dv_j =$$

$$0 \Rightarrow P_j \int L(v_j | \hat{y}_j) dv_j =$$

$$\int L(v_j | \hat{y}_j) v_j v_j^T dv_j - v_j v_j^* \int L(v_j | \hat{y}_j) dv_j \Rightarrow \text{Eq. 26}$$

B. Convexity Proof for Equation (29)

In this section the convexity of the cost function in the ICM scheme $F|z_i^{(k)} = 1$ by calculating the Hessian matrix. From Eq. (29), the Hessian matrix with respect to $w_i$ becomes $$H\left(F|_{z_i^{(k)} = 1}\right) = \sum_{j \in ray'(i)} d_{ij} P_j^{-1} + \sum_{i' \in ne(i)} \beta_1(z_i \cdot z_{i'}) I + \beta_3 \sum_k, \quad (38)$$

where I is the identity matrix. Because each term in Eq. (38) is a covariance matrix, H is positive-semidefinite, i.e., H ≥ 0, therefore $F|z_i^{(k)} = 1$ is convex.

A computing device can be programmed to execute the steps of the method of the present invention. A computing device for use with the present invention can be loaded with a non-transitory computer readable medium configured to execute the steps of the method. Alternately, the computing device can be networked to a server or other computing device configured to execute the steps of the method. The computing device can also be networked to the computed tomography scanning machine either wired or wirelessly in order to obtain the information from the computed tomography scans for processing. The information from the computed tomography scan can also be input into the computing device manually or using magnetic, optical, or other computer readable medium. As used herein, a non-transitory computer readable medium can be any article of manufacture that contains data that can be read by a computer. Such computer readable media includes but is not limited to magnetic media, such as a floppy disk, a flexible disk, a hard disk, reel-to-reel tape, cartridge tape, cassette tape or cards; optical media such as CD-ROM and writeable compact disc; magneto-optical media in disc, tape or card form; and paper media, such as punched cards and paper tape. The computer readable medium contains code such that the method described herein can be executed.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method for joint-estimation of characteristics of tissue types (z) and basis function density images (w) of a subject for x-ray computed tomography (CT) comprising:
    obtaining x-ray projection data at multiple energy settings for the subject;
    executing a joint estimation framework employing a maximum a posteriori (MAP) estimation;
    calculating a latent Markov Random Field (MRF) to describe a geometrical relationship between z and w;
    determining a statistical relationship between z and w;
    generating noise models of the x-ray projection data;
    calculating a Bayesian estimation from the x-ray projection data; and
    generating an image of the subject.

2. The method of claim 1 further comprising acquiring the x-ray projection data using a photon counting detector CT.

3. The method of claim 1 further comprising acquiring the x-ray projection data using dual-energy CT.

4. The method of claim 1 further comprising representing a set of basis functions based on physical phenomenon such as photoelectric effect and Compton scattering coefficients using w.

5. The method of claim 1 further comprising using one selected from a group consisting of Poisson noise models and Gaussian models of photon counting detector (PCD) data.

6. The method of claim 1 further comprising representing a set of basis materials such as water and bone coefficients with w.

7. The method of claim 1 further comprising programming a non-transitory computer readable medium to execute the method.

8. The method of claim 2 further comprising using w to represent a set of photon character (P-C) coefficients on the image of the subject.

9. The method of claim 2 further comprising using z to represent a set of latent variable labels.

10. The method of claim 9 further comprising defining a prior distribution as a combination of the latent Markov Random Field (MRF) and statistical distribution between w and z.

11. A non-transitory computer readable medium configured for executing a method comprising:
    obtaining x-ray projection data at multiple energy settings for a subject;
    executing a joint estimation framework employing a maximum a posteriori (MAP) estimation;
    calculating a latent Markov Random Field (MRF) to describe a geometrical relationship between z and w;
    determining a statistical relationship between z and w;
    generating noise models of the x-ray projection data;
    calculating a Bayesian estimation from the x-ray projection data; and
    generating an image of the subject.

12. The non-transitory computer readable medium of claim 11 further configured for acquiring the x-ray projection data using a photon counting detector CT.

13. The non-transitory computer readable medium of claim 11 further configured for acquiring the x-ray projection data using dual-energy CT.

14. The non-transitory computer readable medium of claim 11 further configured for representing a set of basis functions based on physical phenomenon such as photoelectric effect and Compton scattering coefficients using w.

15. The non-transitory computer readable medium of claim 11 further configured for using one selected from a group consisting of Poisson noise models and Gaussian models of photon counting detector data.

16. The non-transitory computer readable medium of claim 11 further configured for representing a set of basis materials such as water and bone coefficients with w.

17. The non-transitory computer readable medium of claim 12 further configured for further comprising using w to represent a set of photon character (P-C) coefficients on the image of the subject.

18. The non-transitory computer readable medium of claim 12 further configured for using z to represent a set of latent variable labels.

19. The non-transitory computer readable medium of claim 18 further configured for defining a prior distribution as a combination of the latent Markov Random Field (MRF) and statistical distribution between w and z.

* * * * *